United States Patent
Koenemann et al.

(10) Patent No.: US 7,799,920 B2
(45) Date of Patent: Sep. 21, 2010

(54) METHOD FOR PRODUCING PERYLENE-3,4-DICARBOXYLIC ACID IMIDES

(75) Inventors: Martin Koenemann, Mannheim (DE); Peter Blaschka, Ludwigshafen (DE); Helmut Reichelt, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 804 days.

(21) Appl. No.: 11/718,893

(22) PCT Filed: Nov. 4, 2005

(86) PCT No.: PCT/EP2005/011823

§ 371 (c)(1),
(2), (4) Date: May 9, 2007

(87) PCT Pub. No.: WO2006/050860

PCT Pub. Date: May 18, 2006

(65) Prior Publication Data

US 2008/0114170 A1    May 15, 2008

(30) Foreign Application Priority Data

Nov. 9, 2004    (DE)    ........................ 10 2004 054 303

(51) Int. Cl.
C07D 221/18    (2006.01)
C07D 493/02    (2006.01)

(52) U.S. Cl. ........................................ 546/38; 549/232

(58) Field of Classification Search ................... 546/38; 549/232

See application file for complete search history.

(56) References Cited

U.S. PATENT DOCUMENTS 5,808,073 A * 9/1998 Bohm et al. ................... 546/39

FOREIGN PATENT DOCUMENTS

EP    0 657 436    6/1995
WO    96 22331    7/1996

OTHER PUBLICATIONS

Heinz Langhals, et al., "Balanced Decarboxylation of Aromatic Polyacids—A One-Step Synthesis of Perylene-3,4-Dicarboxylic Anhydride", Liebigs Annalen/Recueil, vol. 3, XP 002060924, pp. 467-468, 1997.

* cited by examiner

*Primary Examiner*—Charanjit S Aulakh
(74) *Attorney, Agent, or Firm*—Oblon, Spivak, McClelland, Maier & Neustadt, L.L.P.

(57) ABSTRACT

A process for preparing perylene-3,4-dicarboximides which bear a sterically demanding substituent on the imide nitrogen atom by reacting a perylene-3,4:9,10-tetracarboxylic dianhydride with a sterically hindered primary amine in a substantially anhydrous reaction medium, which comprises undertaking the reaction in the presence of a tertiary amine, of a solvent based on a cyclic imine or amide and of a Lewis acid as a catalyst.

8 Claims, No Drawings

METHOD FOR PRODUCING PERYLENE-3,4-DICARBOXYLIC ACID IMIDES

The present invention relates to a novel process for preparing perylene-3,4-dicarboximides which bear a sterically demanding substituent on the imide nitrogen atom by reacting a perylene-3,4:9,10-tetracarboxylic dianhydride with a sterically hindered primary amine in a substantially anhydrous reaction medium.

Perylene-3,4-dicarboximides are well known to be suitable as fluorescence dyes and pigments, and as intermediates for fluorescence dyes, pigments, pigment additives and IR absorbers.

The perylene-3,4-dicarboximides (N-substituted imides substituted or unsubstituted in the perylene skeleton) may, as described in WO-A-96/22331, be prepared by reacting the perylene-3,4:9,10-tetracarboxylic dianhydrides with primary amines in a substantially anhydrous reaction medium in the presence of a tertiary basic nitrogen compound as a solvent and of a transition metal catalyst.

Suitable tertiary basic nitrogen compounds mentioned here, in addition to tertiary aliphatic amines such as trihexylamine and cyclic amides such as N-methylpyrrolidone, are in particular aromatic heterocyclic imines such as quinoline, isoquinoline and quinaldine. Mixtures of these compounds are not mentioned, and the reactions described by way of example are all undertaken in quinoline.

Although the perylene-3,4-dicarboximides are obtained in high yields in this reaction, their purity is in many cases insufficient especially for use as an intermediate for fluorescence dyes and IR absorbers, so that the purification process which is likewise described in WO-A-96/22331 (conversion of the crude products to N-methylpyrrolidone adducts and treatment of these adducts with bases and, if desired, final treatment of the reisolated products with acids) has to follow the preparation process. This purification process is time-consuming and therefore expensive as a result of the filtration steps to be undertaken.

EP-A-657 436 describes the reaction analogous to WO-A-96/22331, under pressure in the presence of water. However, the yields obtained are only in the range of from 10 to 50%.

It is an object of the invention to provide a process by which perylene-3,4-dicarboximides which bear sterically demanding substituents on the imide nitrogen atom are obtainable in an advantageous manner in high yield and such high purity that an additional purification can be omitted.

Accordingly, a process has been found for preparing perylene-3,4-dicarboximides which bear a sterically demanding substituent on the imide nitrogen atom by reacting a perylene-3,4:9,10-tetracarboxylic dianhydride with a sterically hindered primary amine in a substantially anhydrous reaction medium, which comprises undertaking the reaction in the presence of a tertiary amine, of a solvent based on a cyclic imine or amide and of a Lewis acid as a catalyst.

It is essential for the process according to the invention that a tertiary amine, i.e. an amine bearing 3 substituents (referred to hereinbelow as "aminic catalyst") is used as a catalyst in addition to the cyclic imine.

Suitable aminic catalysts are preferably amines of the general formula I

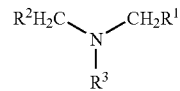

in which the variables are each defined as follows:

$R^1$, $R^2$ are each independently
  hydrogen;
  $C_1$-$C_{23}$-alkyl whose carbon chain may be interrupted by one or more —O—, —S— and/or —$NR^4$— moieties and which may be substituted by hydroxyl, cyano, halogen, nitro, $C_6$-$C_{10}$-aryl which may comprise from one to three heteroatoms in the ring system and/or $C_4$-$C_{12}$-cycloalkyl which may comprise from one to four heteroatoms in the ring system;
  $C_4$-$C_{12}$-cycloalkyl whose carbon ring may be interrupted by one or more —O—, —S— and/or —$NR^4$— moieties and which may be substituted by $C_1$-$C_{18}$-alkyl, hydroxyl, cyano, halogen and/or nitro;
  $C_6$-$C_{10}$-aryl which may be substituted by $C_1$-$C_{18}$-alkyl, hydroxyl, cyano, halogen and/or nitro;
  together are a 4- to 9-membered saturated ring which comprises the —$CH_2$—$NR^3$—$CH_2$— moiety and may be interrupted by further —O—, —S— and/or —$NR^4$— moieties and may be substituted by $C_1$-$C_6$-alkyl, $C_6$-$C_{10}$-aryl, hydroxyl, cyano, halogen and/or nitro;

$R^3$ is $C_4$-$C_{24}$-alkyl, whose carbon chain may be interrupted by one or more —O—, —S— and/or —$NR^4$— moieties and which may be substituted by hydroxyl, cyano, nitro, $C_6$-$C_{10}$aryl which may comprise from one to three heteroatoms in the ring system and/or $C_4$-$C_{12}$-cycloalkyl which may comprise from one to four heteroatoms in the ring system;
  $C_4$-$C_{12}$-cycloalkyl whose carbon chain may be interrupted by one or more —O—, —S— and/or —$NR^4$— moieties and which may be substituted by $C_1$-$C_{18}$-alkyl, hydroxyl, cyano, halogen and/or nitro;
  $C_6$-$C_{10}$-aryl which may comprise from one to three heteroatoms in the ring system and which may be substituted by $C_1$-$C_{18}$-alkyl, hydroxyl, cyano and/or nitro;

$R^1$, $R^2$ and $R^3$ join together to form a saturated, bicyclic 8- to 12-membered ring system which comprises the

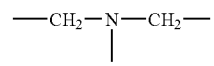

moiety and if appropriate further —O—, —S— and/or —$NR^4$— moieties;

$R^4$ is hydrogen; $C_1$-$C_{12}$-alkyl.

Particular preference is given to aminic catalysts of the formula I in which the variables are each defined as follows:

$R^1$, $R^2$ are each independently
  hydrogen;
  $C_1$-$C_{11}$-alkyl which may be substituted by hydroxyl;
  together are a 4- to 9-membered saturated ring which comprises the —$CH_2$—$NR^3$—$CH_2$— moiety and may be interrupted by further —$NR^4$— moieties;

$R^3$ is $C_4$-$C_{12}$-alkyl which may be substituted by hydroxyl; pyridyl;

$R^1$, $R^2$ and $R^3$ join together to form a bicyclic 8-membered ring system which comprises the

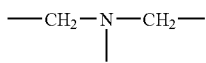

moiety and one further nitrogen atom;

$R^4$ is hydrogen; $C_1$-$C_{12}$-alkyl.

The process according to the invention is preferably used to prepare perylene-3,4-dicarboximides of the general formula II

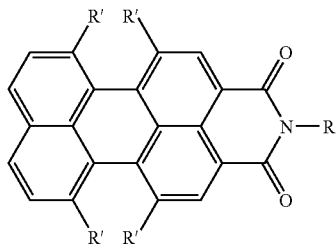

II in which the variables are each defined as follows:

R is $C_3$-$C_{24}$-alkyl which is branched in the 1-position and whose carbon chain may be interrupted by one or more —O—, —S—, —NR$^4$—, —CO— and/or —SO$_2$— moieties and which may be mono- or polysubstituted by carboxyl, sulfo, hydroxyl, cyano, $C_1$-$C_6$-alkoxy, $C_3$-$C_8$-cycloalkyl which may comprise from one to four heteroatoms in the ring system and/or $C_6$-$C_{10}$-aryl which may comprise from one to three heteroatoms in the ring system;

phenyl which is substituted in the ortho-position by at least one of the substituents (a) to (e) and may bear the same or one or more different substituents in the further ring positions and which may comprise one or two heteroatoms in the ring:

(a) $C_1$-$C_{24}$-alkyl whose carbon chain may be interrupted by one or more —O—, —S—, —NR$^4$—, —CO— and/or —SO$_2$— moieties and which may be mono- or polysubstituted by carboxyl, sulfo, hydroxyl, cyano, halogen, nitro, $C_1$-$C_6$-alkoxy, $C_3$-$C_8$-cycloalkyl which may comprise from one to four heteroatoms in the ring system and/or $C_6$-$C_{10}$-aryl which may comprise from one to three heteroatoms in the ring system;

(b) $C_1$-$C_{24}$-alkoxy or $C_1$-$C_{24}$-alkylthio, each of which may be mono- or polysubstituted by $C_1$-$C_6$-alkyl and/or phenyl;

(c) $C_3$-$C_8$-cycloalkyl which may comprise from one to four heteroatoms in the ring system, may comprise unsaturated bonds and may be mono- or polysubstituted by carboxyl, sulfo, hydroxyl, cyano, halogen, nitro, $C_1$-$C_6$-alkoxy and/or $C_6$-$C_{10}$-aryl which may comprise from one to three heteroatoms in the ring system;

(d) $C_6$-$C_{10}$-aryl which may comprise from one to three heteroatoms in the ring system, to which further 5- to 7-membered, saturated, unsaturated or aromatic rings may be fused and which may be mono- or polysubstituted by $C_1$-$C_{12}$-alkyl;

(e) carboxyl, hydroxyl, cyano, halogen, nitro, —SO$_2$NR$^4{}_2$;

1-naphthyl which is substituted in the ortho-position by one of the substituents (a) to (e) specified for phenyl and may bear in the further ring positions the same or one or more different substituents and which may comprise from one to three heteroatoms in the ring system;

2-naphthyl which is substituted in both ortho-positions by one of the substituents (a) to (e) specified for phenyl or different substituents from this group and may bear in the further ring positions the same or one or more different substituents and which may comprise from one to three heteroatoms in the ring system;

R' are each independently hydrogen; halogen; $C_1$-$C_{18}$-alkyl; $C_6$-$C_{10}$-aryloxy or -arylthio, each of which may comprise from one to three heteroatoms in the ring system and each of which may be substituted by $C_1$-$C_{10}$-alkyl, $C_1$-$C_6$-alkoxy, cyano and/or carboxyl;

$R^4$ is hydrogen; $C_1$-$C_{12}$-alkyl, by reacting a perylene-3,4:9,10-tetracarboxylic dianhydride of the general formula III

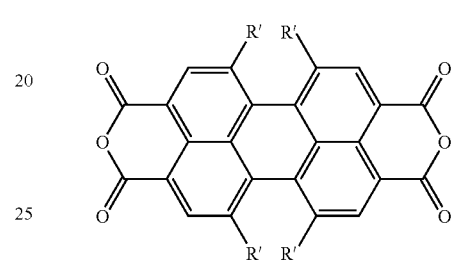

III with a primary amine of the general formula IV

 R—NH$_2$  IV

Particular preference is given to using the process according to the invention to pre-pare perylene-3,4-dicarboximides of the general formula II in which the variables are each defined as follows:

R is $C_3$-$C_{24}$-alkyl which is branched in the 1-position;

phenyl which is substituted in both ortho-positions by secondary $C_3$-$C_{12}$-alkyl radicals or in one ortho-position by a tertiary $C_4$-$C_{12}$-alkyl radical and which may be substituted in the other positions by $C_1$-$C_{12}$-alkyl, $C_6$-$C_{10}$-aryl and/or halogen;

R' is hydrogen; halogen; $C_6$-$C_{10}$-aryloxy or -arylthio, each of which may be substituted by $C_1$-$C_{10}$-alkyl, $C_1$-$C_6$-alkoxy, cyano and/or carboxyl.

Specific examples of the R, R' and $R^1$ to $R^4$ radicals mentioned in the formulae I to IV and their substituents are as follows:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetraoxatetradecyl; 2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

formylamino, acetylamino, propionylamino and benzoylamino;

chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

2-dioxanyl, 4-morpholinyl, 2- and 3-tetrahydrofuryl, 1-, 2- and 3-pyrrolidinyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

Specific examples of suitable aminic catalysts are listed hereinbelow, and particularly suitable amines have a boiling point above the reaction temperature:

reaction products of ammonia, monoalkylamines, dialkylamines, arylamines, alkylarylamines and cyclic dialkylamines, whose alkyl radicals preferably have from 2 to 24, in particular from 2 to 12, carbon atoms and whose aryl radicals have preferably from 6 to 10, in particular 6, carbon atoms, with alkylene oxides and arylene oxides, preferably $C_2$-$C_{12}$-alkylene oxides, especially $C_2$-$C_6$-alkylene oxides, in particular $C_2$-$C_3$-alkylene oxides, particular preference being given to the reaction products of dialkylamines and monoalkylamines with alkylene oxides:

N,N-diethylethanolamine, N,N-dibutylethanolamine, N,N-dipentylethanolamine, N,N-dihexylethanolamine, N,N-dioctylethanolamine, N,N-didodecylethanolamine, N,N-dioctadecylethanolamine, triethanolamine, 1-diethylaminopropan-2-ol, 1-diethylaminobutan-2-ol, 1-diethylaminopentan-2-ol, 1-diethylaminododecan-2-ol, 1-diethylaminooctadecan-2-ol, 1-dipropylaminopropan-2-ol, 1-dipropylaminobutan-2-ol, 1-dipropylaminopentan-2-ol, 1-dipropylaminododecan-2-ol, 1-dipropylaminooctadecan-2-ol, 1-dibutylaminopropan-2-ol, 1-dibutylaminobutan-2-ol, 1-dibutylaminopentan-2-ol, 1-dibutylaminododecan-2-ol and 1-dibutylaminooctadecan-2-ol;

N,N-(di-2-hydroxyethyl)butylamine, N,N-(di-2-hydroxyethyl)hexylamine, N,N-(di-2-hydroxyethyl)octylamine, N,N-(di-2-hydroxyprop-2-yl)butylamine, N,N-(di-2-hydroxyprop-2-yl)hexylamine and N,N-(di-2-hydroxyprop-2-yl)octylamine;

N-phenyldiethanolamine, N-(p-tolyl)diethanolamine, N-phenyldi(2-propanol)amine, N-(p-tolyl)di(2-propanol)amine, N-phenyldi(2-butanol)amine and N-(p-tolyl)di(2-butanol)amine;

trialkylamines whose alkyl radicals have from 3 to 24, in particular from 3 to 12, carbon atoms:

tripropylamine, tributylamine, tripentylamine, trihexylamine, triheptylamine, trioctylamine, trinonylamine, tridecylamine, tridodecylamine, trioctadecylamine, diethylpropylamine, dipropylbutylamine, dibutylpentylamine, dihexylheptylamine, dimethyl(2-ethylhexyl)amine and dimethyl(3-propylheptyl)amine;

cyclic trialkylamines:

N-alkylmorpholines such as N-methylmorpholine; 1,4-diazabicyclo[2.2.2]octane (DABCO); N,N'-dialkylpiperazines such as N,N'-dimethylpiperazine; N,N'-diarylpiperazines such as N,N'-diphenylpiperazine; N-alkyl-N'-arylpiperazines such as N-phenyl-N'-methylpiperazine;

dialkylarylamines:

dimethylaniline, diethylaniline, dipropylaniline and dibutylaniline;

dialkylaminoheteroaromatics, preferably 4-(N,N-(di-$C_1$-$C_4$-alkyl)amino)pyridines, and heteroaromatics substituted by cyclic amino groups:

4-(N,N-dimethylamino)pyridine (DMAP), 4-(N,N-diethylamino)pyridine and 4-(N,N-dipropylamino)pyridine; 4-pyrrolidin-1-ylpyridine and 4-piperidin-1-ylpyridine.

Preferred aminic catalysts are the reaction products of mono- and dialkylamines with ethylene oxide and/or propylene oxide, cyclic trialkylamines and dialkylaminoheteroaromatics and heteroaromatics substituted by cyclic amino groups.

Particular preference is given to $C_3$-$C_6$-dialkylethanolamines, e.g. dibutylethanolamine, $C_3$-$C_{10}$-alkyldiethanolamines and in particular -dipropanolamines, e.g. octyldipropanolamine, 1,4-diazabicyclo[2.2.2]octane and 4-(N,N-(di-$C_1$-$C_4$-alkyl)amino)pyridines, e.g. 4-(N,N-dimethylamino) pyridine, 4-pyrrolidin-1-ylpyridine and 4-piperidin-1-ylpyridine.

It will be appreciated that it is also possible to use mixtures of the aminic catalysts.

In general, from 0.01 to 4 mol, preferably from 0.5 to 2 mol, of aminic catalyst are used per mole of perylene-3,4:9,10-tetracarboxylic dianhydride.

The solvents used in the process according to the invention are cyclic imines or amides. In addition to cyclic amides such as N-methylpyrrolidone, suitable solvents are in particular cyclic imines such as quinoline, isoquinoline and quinaldine, of which quinoline is the preferred solvent. It will be appreciated that it is also possible to use solvent mixtures.

The amount of solvent is not critical per se and is typically from 2 to 20 kg, preferably from 1 to 8 kg, per kg of perylene-3,4:9,10-tetracarboxylic dianhydride.

A further catalyst used in the process according to the invention is a Lewis acid. It is preferably a transition metal catalyst based on iron and in particular zinc or copper. Particular preference is given to the inorganic and the organic salts of these metals. It will be appreciated that it is also possible to use mixtures of these catalysts.

Examples of preferred salts are copper(I) oxide, copper(II) oxide, copper(I) chloride, copper(II) acetate, zinc acetate and zinc propionate.

In general, from 0.1 to 10 molar equivalents, preferably from 0.5 to 3 molar equivalents, of Lewis acid catalyst based on the perylene-3,4:9,10-tetracarboxylic dianhydride are used.

In the process according to the invention, a substantially anhydrous reaction medium is used. In other words, water of reaction released in the course of the reaction is distilled off continuously or driven out by a carrier gas stream, for example a nitrogen stream, and all reaction components are used in substantially anhydrous form. However, it is also possible to distill off water present in the reaction components, for example water of hydration of catalyst salts, during the reaction.

The primary amines used in the process according to the invention are sterically hindered primary amines, in particular the amines of the formula IV.

In general, from 1 to 6 mol, preferably from 1.5 to 4 mol, of primary amine are used per mole of perylene-3,4:9,10-tetracarboxylic dianhydride.

The reaction temperature is generally from 120 to 250° C., preferably from 180 to 250° C.

It is recommended to work using a protective gas atmosphere (for example nitrogen).

Typically, the inventive reaction is complete within from 2 to 40 h, in particular within from 5 to 30 h.

In terms of process operation, the procedure in the process according to the invention is appropriately as follows:

Perylene-3,4:9,10-tetracarboxylic dianhydride, Lewis acid catalyst, primary amine and aminic catalyst are introduced into the solvent, the apparatus is purged with nitrogen and the mixture is heated with stirring to the reaction temperature. In the course of this, water of reaction which forms and any water present in the reaction components used is distilled off. After stirring at the reaction temperature for from about 5 to 30 hours, the mixture is cooled to from 50 to 80° C. and diluted by adding a primary aliphatic alcohol, for example methanol, ethanol, propanol or ethylene glycol.

The perylene-3,4-dicarboximide precipitated in this way may be isolated by filtration. To remove a metallic Lewis acid catalyst, it may be extracted by stirring in inorganic acid (for example from 5 to 20% by weight hydrochloric acid or sulfuric acid) at from 50 to 80° C. This treatment may also be undertaken in combination with a primary aliphatic alcohol such as ethanol. The product which has been filtered off is finally typically washed with ethanol and water, and dried.

The perylene-3,4-dicarboximides obtained in this way have such high purities (generally >94%) that they generally do not have to be subjected to any further purification and can be used directly for all purposes.

The process according to the invention is suitable in an excellent manner for the preparation of all perylene-3,4-dicarboximides which bear sterically hindered substituents on the imide nitrogen atom. It is possible to prepare perylene-3,4-dicarboximides which are either substituted or unsubstituted in the rylene ring in high yields (typically from 45 to 65%).

EXAMPLES

Example 1

400 g (1 mol) of perylene-3,4:9,10-tetracarboxylic dianhydride and 400 g (1.8 mol) of zinc acetate were added with vigorous stirring to a mixture of 1500 ml of quinoline, 585 g (3 mol) of diisopropylaniline and 294 g (1.2 mol) of N,N-(di-2-hydroxyprop-2-yl)octylamine. The mixture was then heated to 21° C. and stirred at this temperature for 30 h. In the course of this, about 50 ml of water distilled off.

After the quinoline had been distilled off, the residue was stirred twice at 70° C. with 2000 g of 20% by weight sulfuric acid, filtered off and washed first with water and then with ethanol until the filtrate was colorless, and then dried.

258 g of N-(2,6-diisopropylphenyl)perylene-3,4-dicarboximide having a purity of 95% were obtained, which corresponds to a yield of 51%.

Example 2

400 g (1 mol) of perylene-3,4:9,10-tetracarboxylic dianhydride and 395 g (1.8 mol) of anhydrous zinc acetate were added with vigorous stirring to a mixture of 1500 ml of quinoline, 585 g (3 mol) of diisopropylaniline and 200 g (1.2 mol) of N,N-dibutylethanolamine. The mixture was then heated to 215° C. and stirred at this temperature for 28 h. In the course of this, about 50 ml of water distilled off.

After some of the quinoline had been distilled off, and the mixture had been cooled to 75° C. and diluted with 1400 ml of ethanol, the precipitated product was filtered off and stirred at 70° C. first with about 2 l of ethanol and then repeatedly with a total of 4400 g of 16% by weight sulfuric acid, and finally washed to neutrality with water and dried under reduced pressure.

247 g of N-(2,6-diisopropylphenyl)perylene-3,4-dicarboximide having a purity of 96% were obtained, which corresponds to a yield of 50%.

Example 3

40 g (0.1 mol) of perylene-3,4:9,10-tetracarboxylic dianhydride were added with vigorous stirring to a mixture of 100 ml of quinoline, 58.5 g (0.3 mol) of 2,6-diisopropylaniline and 13.4 g (0.12 mol) of 1,4-diazabicyclo[2.2.2]octane and 14.3 g (0.18 mol) of copper(II) oxide. The mixture was then heated to 200° C. for 20 h under a gentle nitrogen stream to drive out the water of reaction.

After the quinoline had been distilled off under slightly reduced pressure, the residue was stirred at 50° C. in a mixture of 40 ml of 20% by weight sulfuric acid and about 200 ml of ethanol. After cooling to room temperature, the product was filtered off, stirred once again at 50° C. in fresh sulfuric acid/ethanol mixture, filtered off again and washed repeatedly with ethanol at room temperature. After final washing with water, the product was dried under reduced pressure.

24.1 g of N-(2,6-diisopropylphenyl)perylene-3,4-dicarboximide having a purity of 94% were obtained, which corresponds to a yield of 47%.

What is claimed is:
1. A process for preparing perylene-3,4-dicarboximides which bear a sterically demanding substituent on the imide nitrogen atom and have the general formula II

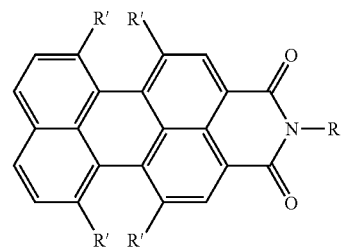

in which the variables are each defined as follows:
is $C_3$-$C_{24}$-alkyl which is branched in the 1-position and whose carbon chain may be interrupted by one or more —O—, —S—, —CO— and/or —SO$_2$— moieties and which may be mono- or polysubstituted by carboxyl, sulfo, hydroxyl, cyano, $C_1$-$C_6$-alkoxy, $C_3$-$C_8$-cycloalkyl which may comprise from one to four heteroatoms in the ring system and/or $C_6$-$C_{10}$-aryl which may comprise from one to three heteroatoms in the ring system;
phenyl which is substituted in the ortho-position by at least one of the substituents (a) to (e) and may bear the same or one or more different substituents (a) to (e) in the further ring positions and which may comprise one or two heteroatoms in the ring:
(a) $C_1$-$C_{24}$-alkyl whose carbon chain may be interrupted by one or more —O—, —S—, —NR$^4$—, —CO— and/or —SO$_2$— moieties and which may be mono- or polysubstituted by carboxyl, sulfo, hydroxyl, cyano, halogen, nitro, $C_1$-$C_6$-alkoxy, $C_3$-$C_8$-cycloalkyl which may comprise from one to four heteroatoms in the ring system and/or $C_6$-$C_{10}$-aryl which may comprise from one to three heteroatoms in the ring system;
(b) $C_1$-$C_{24}$-alkoxy or $C_1$-$C_{24}$-alkylthio, each of which may be mono- or polysubstituted by $C_1$-$C_6$-alkyl and/or phenyl;
(c) $C_3$-$C_8$-cycloalkyl which may comprise from one to four heteroatoms in the ring system, may comprise unsaturated bonds and may be mono- or polysubstituted by carboxyl, sulfo, hydroxyl, cyano, halogen, nitro, $C_1$-$C_6$-alkoxy and/or $C_6$-$C_{10}$-aryl which may comprise from one to three heteroatoms in the ring system;
(d) $C_6$-$C_{10}$-aryl which may comprise from one to three heteroatoms in the ring system, to which further 5- to 7-membered, saturated, unsaturated or aromatic rings may be fused and which may be mono- or polysubstituted by $C_1$-$C_{12}$-alkyl;
(e) carboxyl, hydroxyl, cyano, halogen, nitro, —SO$_7$NR$^4{}_2$;
1-naphthyl which is substituted in the ortho-position by one of the substituents (a) to (e) specified for phenyl and may bear in the further ring positions the same or one or more different substituents (a) to (e) and which may comprise from one to three heteroatoms in the ring system;
2-naphthyl which is substituted in both ortho-positions by one of the substituents (a) to (e) specified for phenyl or different substituents from this group and may bear in the further ring positions the same or one or more different substituents (a) to (e) and which may comprise from one to three heteroatoms in the ring system;

R' are each independently hydrogen; halogen; $C_1$-$C_{18}$-alkyl; $C_6$-$C_{10}$-aryloxy or -arylthio, each of which may comprise from one to three heteroatoms in the ring system and each of which may be substituted by $C_1$-$C_{10}$-alkyl, $C_1$-$C_6$-alkoxy, cyano and/or carboxyl;

$R^4$ is hydrogen; $C_1$-$C_{12}$-alkyl, by reacting a perylene-3,4:9,10-tetracarboxylic dianhydride of the general formula III

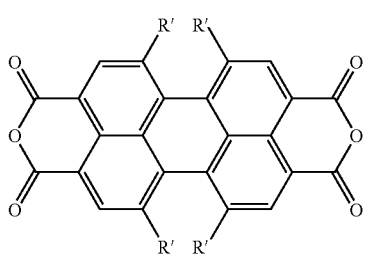

with a sterically hindered primary amine of the general formula IV

    IV in a substantially anhydrous reaction medium, which comprises undertaking the reaction in the presence of a tertiary amine, of a solvent based on a cyclic imine or amide and of a Lewis acid as a catalyst.

2. The process according to claim 1, wherein the tertiary amine used is an amine of the general formula I

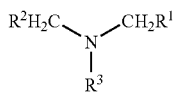    I in which the variables are each defined as follows:
$R^1$, $R^2$ are each independently
  hydrogen;
  $C_1$-$C_{23}$-alkyl whose carbon chain may be interrupted by one or more —O—, —S— and/or —$NR^4$— moieties and which may be substituted by hydroxyl, cyano, halogen, nitro, $C_6$-$C_{10}$-aryl which may comprise from one to three heteroatoms in the system and/or $C_4$-$C_{12}$-cycloalkyl which may comprise from one to four heteroatoms in the ring system;
  $C_4$-$C_{12}$-cycloalkyl whose carbon ring may be interrupted by one or more —O—, —S— and/or —$NR^4$— moieties and which may be substituted by $C_1$-$C_{18}$-alkyl, hydroxyl, cyano, halogen and/or nitro;
  $C_6$-$C_{10}$-aryl which may be substituted by $C_1$-$C_{18}$-alkyl, hydroxyl, cyano, halogen and/or nitro;
  together are a 4- to 9-membered saturated ring which comprises the —$CH_2$—$NR^3$—$CH_2$— moiety and may be interrupted by further —O—, —S— and/or —$NR^4$— moieties and may be substituted by $C_1$-$C_6$-alkyl, $C_6$-$C_{10}$-aryl, hydroxyl, cyano, halogen and/or nitro;
$R^3$ is $C_4$-$C_{24}$-alkyl, whose carbon chain may be interrupted by one or more —O—, —S— and/or —$NR^4$— moieties and which may be substituted by hydroxyl, cyano, nitro, $C_6$-$C_{10}$-aryl which may comprise from one to three heteroatoms in the ring system and/or $C_4$-$C_{12}$-cycloalkyl which may comprise from one to four heteroatoms in the ring system;
  $C_4$-$C_{12}$-cycloalkyl whose carbon ring may be interrupted by one or more —O—, —S— and/or —$NR^4$— moieties and which may be substituted by $C_1$-$C_{18}$-alkyl, hydroxyl, cyano, halogen and/or nitro;
  $C_6$-$C_{10}$-aryl which may comprise from one to three heteroatoms in the ring system and which may be substituted by $C_1$-$C_{18}$-alkyl, hydroxyl, cyano and/or nitro;
$R^1$, $R^2$ and $R^3$ join together to form a saturated, bicyclic 8- to 12-membered ring system which comprises the

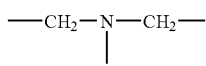

moiety and if appropriate further —O—, —S— and/or —$NR^4$— moieties;
$R^4$ is hydrogen; $C_1$-$C_{12}$-alkyl.

3. The process according to claim 1, wherein the tertiary amine used is an amine of the general formula I

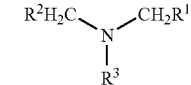    I in which the variables are each defined as follows:
$R^1$, $R^2$ are each independently
  hydrogen;
  $C_1$-$C_{11}$-alkyl which may be substituted by hydroxyl;
  together are a 4- to 9-membered saturated ring which comprises the —$CH_2$—$NR^3$—$CH_2$— moiety and may be interrupted by further —$NR^4$— moieties;
$R^3$ is $C_4$-$C_{12}$-alkyl which may be substituted by hydroxyl; pyridyl;
$R^1$, $R^2$ and $R^3$ join together to form a bicyclic 8-membered ring system which comprises the

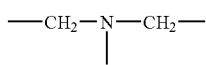

moiety and one further nitrogen atom;
$R^4$ is hydrogen; $C_1$-$C_{12}$-alkyl.

4. The process according to claim 1, wherein the tertiary amine used is an amine whose boiling point is above the reaction temperature.

5. The process according to claim 1, wherein the cyclic imine used is a cyclic aromatic imine.

6. The process according to claim 1, wherein the Lewis acid used is a transition metal catalyst based on iron, zinc, zinc salts, copper, copper salts or mixtures thereof.

7. The process according to claim 1, wherein from 0.01 to 4 mol of tertiary amine are used per mole of perylene-3,4:9, 10-tetracarboxylic dianhydride.

8. The process according to claim 1, wherein the perylene-3,4-dicarboximides of the general formula II is prepared

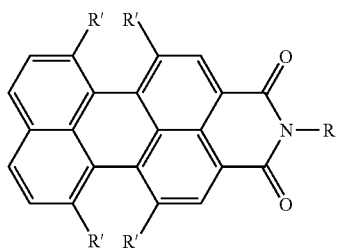

II in which the variables are each defined as follows:

R is $C_3$-$C_{24}$-alkyl which is branched in the 1-position;
phenyl which is substituted in both ortho-positions by secondary $C_3$-$C_{12}$-alkyl radicals or in one ortho-position by a tertiary $C_4$-$C_{12}$-alkyl radical and which may be substituted in the other positions by $C_1$-$C_{12}$-alkyl, $C_6$-$C_{10}$-aryl and/or halogen;

R' is hydrogen; halogen; $C_6$-$C_{10}$-aryloxy or -arylthio, each of which may be substituted by $C_1$-$C_{10}$-alkyl, $C_1$-$C_6$-alkoxy, cyano and/or carboxyl.

* * * * *